US012480296B2

(12) United States Patent
Momose

(10) Patent No.: US 12,480,296 B2
(45) Date of Patent: Nov. 25, 2025

(54) BATHTUB DRAINAGE DEVICE

(71) Applicant: Ayako Momose, Kanagawa (JP)

(72) Inventor: Ayako Momose, Kanagawa (JP)

( * ) Notice: Subject to any disclaimer, the term of this patent is extended or adjusted under 35 U.S.C. 154(b) by 80 days.

(21) Appl. No.: 18/602,131

(22) Filed: Mar. 12, 2024

(65) Prior Publication Data

US 2024/0209606 A1 Jun. 27, 2024

Related U.S. Application Data

(63) Continuation of application No. PCT/JP2021/034256, filed on Sep. 17, 2021.

(51) Int. Cl.
*E03C 1/23* (2006.01)
*A61B 5/00* (2006.01)

(52) U.S. Cl.
CPC .......... *E03C 1/2302* (2013.01); *A61B 5/0077* (2013.01); *A61B 5/6887* (2013.01); *E03C 2001/2313* (2013.01)

(58) Field of Classification Search
CPC . E03C 1/2302; E03C 1/22; E03C 1/23; A61G 7/1003; A61G 7/1005
See application file for complete search history.

(56) References Cited

U.S. PATENT DOCUMENTS 6,363,545 B1 * 4/2002 Nowosad ............. A61G 7/1015 4/565.1
10,314,440 B2 * 6/2019 Rochette ............... E03C 1/2302
11,085,178 B1 * 8/2021 Oliver .................... A47K 3/006

FOREIGN PATENT DOCUMENTS

| | | | |
|---|---|---|---|
| CN | 106859445 | A | 6/2017 |
| JP | H04-108450 | A | 4/1992 |
| JP | 2001-120634 | A | 5/2001 |
| JP | 2003-343907 | A | 12/2003 |
| JP | 6025281 | B1 | 11/2016 |

OTHER PUBLICATIONS

WIPO, International Search Report for International Application No. PCT/JP2021/034256, Nov. 9, 2021.
WIPO, Written Opinion for International Application No. PCT/JP2021/034256, Nov. 9, 2021.

* cited by examiner

*Primary Examiner* — Janie M Loeppke

(57) ABSTRACT

A bathtub drainage device comprises: a plate, that can open and close an opening formed at a position corresponding to a position where a bather can sit on a floor of a bathtub in which hot water is stored, the plate on which at least buttocks of the bather can be placed; a rising part, that raises the plate closing the opening so that the opening is opened; an acquisition unit, that acquires information indicating a state of the bather; and a control unit, that controls the rising part so as to raise the plate so that the opening is opened and so as to discharge, from the opening, the hot water stored in the bathtub, when the information acquired by the acquisition unit indicates an abnormal state of the bather.

5 Claims, 4 Drawing Sheets

BATHTUB DRAINAGE DEVICE

TECHNICAL FIELD

The technique of the present disclosure relates to a bathtub drainage device.

BACKGROUND

Japanese Patent Application Laid-Open No. 2003-343907 suggests a bath heater with a forced draining function. In the bath heater with a forced draining function, when it is determined that a submersion accident has occurred in a bathtub, a drain in the bathtub is unplugged, in order to prevent accidents such as losing consciousness in the bathtub and getting submerged and drowned while taking a bath.

SUMMARY

However, in the bath heater with the forced draining function, the drain in the bathtub is merely unplugged. Therefore, it takes time for a liquid level of hot water with respect to a face of a bather to be lowered.

It is an object of the technique of the present disclosure to provide a bathtub drainage device capable of relatively lowering the liquid level of the hot water with respect to the face of the bather more quickly than the background technique.

In order to achieve the above object, the bathtub drainage device of the technique of the present disclosure comprises: a plate, that can open and close an opening formed at a position corresponding to a position where a bather can sit on a floor of a bathtub in which hot water is stored, the plate on which at least buttocks of the bather can be placed; a rising part, that raises the plate closing the opening so that the opening is opened; an acquisition unit, that acquires information indicating a state of the bather; and a control unit, that controls the rising part so as to raise the plate so that the opening is opened and so as to discharge, from the opening, the hot water stored in the bathtub, when the information acquired by the acquisition unit indicates an abnormal state of the bather.

The technique of the present disclosure is capable of relatively lowering the liquid level of the hot water with respect to the face of the bather more quickly than the background technique.

DESCRIPTION

Hereinafter, an embodiment of the technique of the present disclosure will be described with reference to the drawings.

Figure 1:
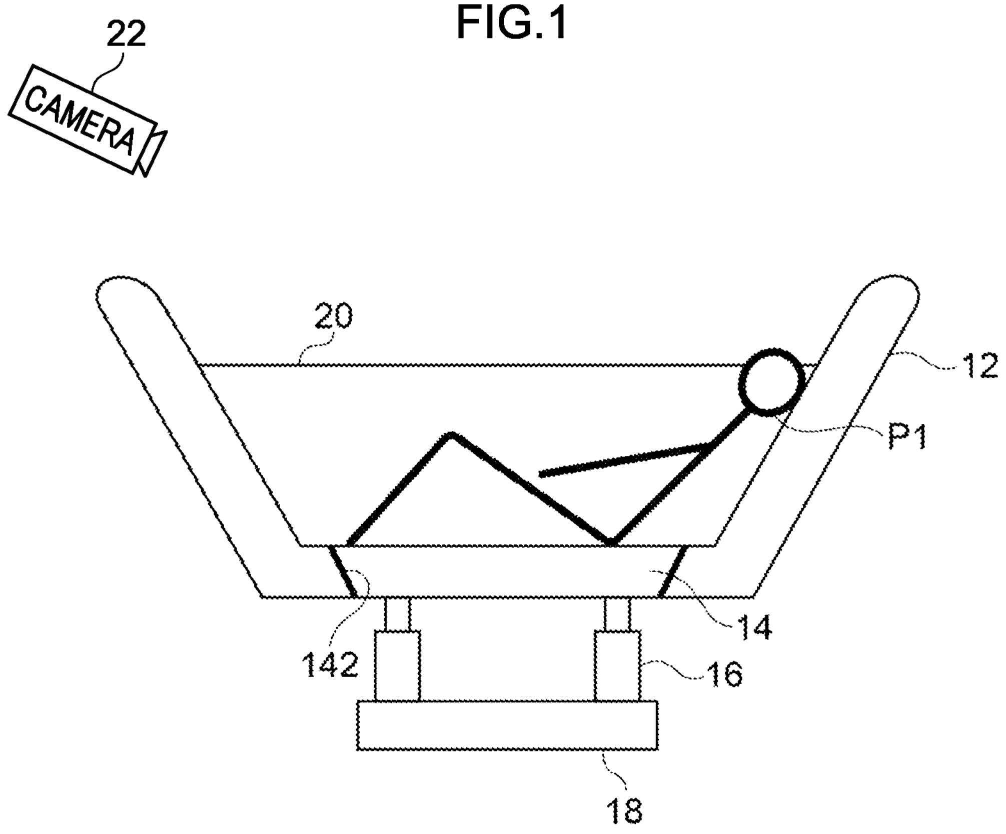
FIG. 1 is a schematic diagram of the bathtub drainage device in the present embodiment.

As shown in FIG. 1, the bathtub drainage device of the present embodiment includes a plate 14. The plate 14 can open and close an opening formed at a position corresponding to a position where a bather can sit on a floor of a bathtub 12 in which hot water 20 is stored. On the plate 14, at least buttocks of the bather can be placed.

The bathtub drainage device includes a sealing member 142 disposed between the opening and the plate 14, specifically, on side surfaces of the plate 14. When the plate 14 wherein the sealing member 142 is disposed on the side surfaces fits into the opening, the opening is closed by the plate 14 and the sealing member 142, and the hot water 20 can be stored in the bathtub 12. Hereinafter, a case where the hot water 20 is stored in the bathtub 12 and the buttocks of the bather are placed on the plate 14 will be described.

The plate 14 has almost the entire size of the floor of the bathtub 12. The shape of an upper surface of the plate 14 corresponds to the shape of the floor of the bathtub 12, and is a rectangle. The size of the plate 14 may be a size enough to support buttocks of a bather with a normal build.

Figure 4:
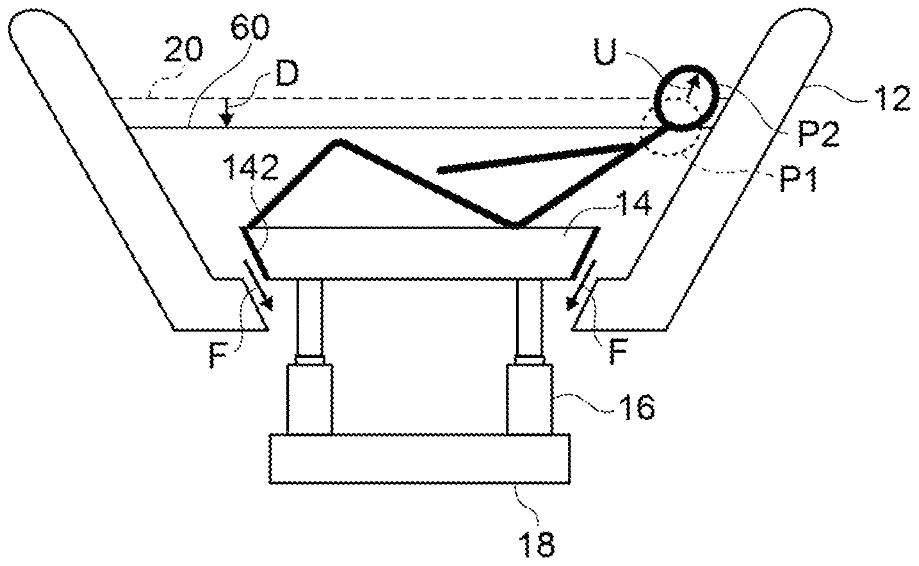
FIG. 4 is a figure showing that, when it is determined that a state of a bather is an abnormal state, a plate 14 on which the bather sits is raised so that an opening is opened, and hot water 20 stored in a bathtub 12 is discharged from the opening.

The bathtub drainage device includes a rising part 16, which raises the plate 14 closing the opening so that the opening is opened. The rising part 16 is composed of, for example, a hydraulic actuator, specifically, four hydraulic cylinders. An upper surface of each hydraulic cylinder 16 is located inward at a predetermined distance from each corner of the rectangular plate 14. When oil is supplied from a hydraulic circuit 18 to each hydraulic cylinder 16, the upper surface of each hydraulic cylinder 16 raises a portion of the rectangular plate 14, being inward at the predetermined distance from each corner thereof, and the plate 14 rises (see also FIG. 4).

The bathtub drainage device includes a camera 22, which acquires information indicating a state of the bather. In an example shown in FIG. 1, the bather takes a bath so that his/her face is located on a right side of the bathtub 12 in FIG. 1 and his/her feet are located on a left side of the bathtub 12 in FIG. 1. The camera 22 photographs the right side of the bathtub 12 in FIG. 1. Therefore, the camera 22 can photograph the face of the bather and can acquire an image of the face showing the state of the bather.

In the technique of the present disclosure, unlike the example shown in FIG. 1, the camera 22 may be disposed at a position where the camera 22 can photograph the left side of the bathtub 12 in FIG. 1, in response to a case where the bather takes a bath so that his/her face is located on the left side of the bathtub 12 in FIG. 1 and his/her feet are located on the right side of the bathtub 12 in FIG. 1. Further, in the technique of the present disclosure, the camera 22 may be disposed at each of the position where the camera 22 can photograph the right side of the bathtub 12 in FIG. 1 and the position where the camera 22 can photograph the left side of the bathtub 12 in FIG. 1.

The camera 22 is an example of "an acquisition unit" of the technology of the present disclosure.

Figure 2:
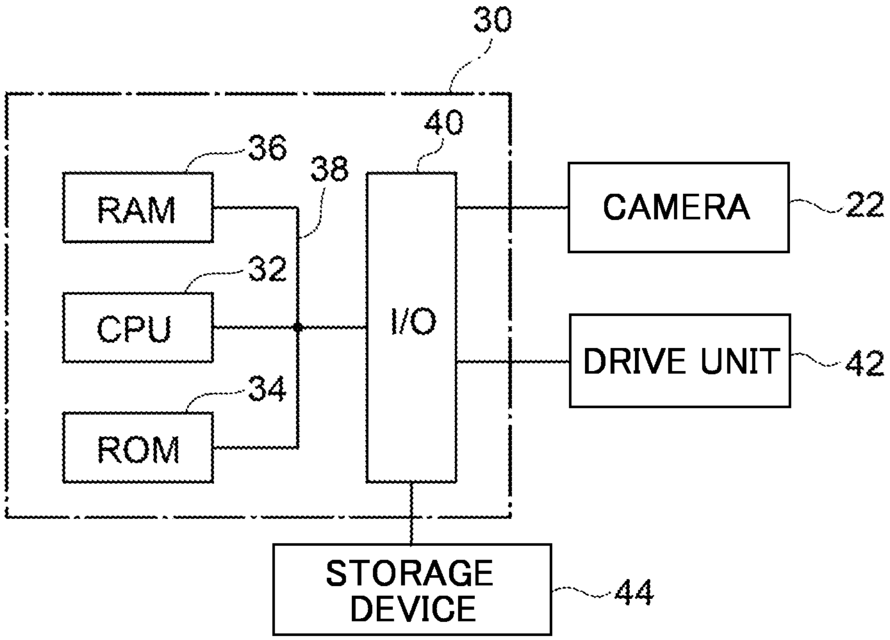
FIG. 2 is a block diagram of a control device 30.

As shown in FIG. 2, the bathtub drainage device includes a control device 30. When the information acquired by the camera 22 (i.e., the image of the face) indicates an abnormal state of the bather, the control device 30 controls the rising part 16 so as to raise the plate 14 so that the opening is opened (see also FIG. 4), and so as to discharge, from the opening, the hot water 20 stored in the bathtub 12 (see arrows F in FIG. 4). As shown in FIG. 2, the control device 30 is composed of a computer. Specifically, the control device 30 includes a CPU 32, a ROM 34, a RAM 36, and an input/output (I/O) port 40, which are interconnected by a bus 38. A storage device 44, the camera 22, and a drive unit 42 are connected to the I/O port 40. The drive unit 42 controls the hydraulic circuit 18 so that oil is supplied to each hydraulic cylinder 16 and the supplied oil returns from each hydraulic cylinder 16, according to the control of the control device 30.

A bathtub drainage treatment program described later is stored in the ROM 34 or the storage device 44.

Figure 3:
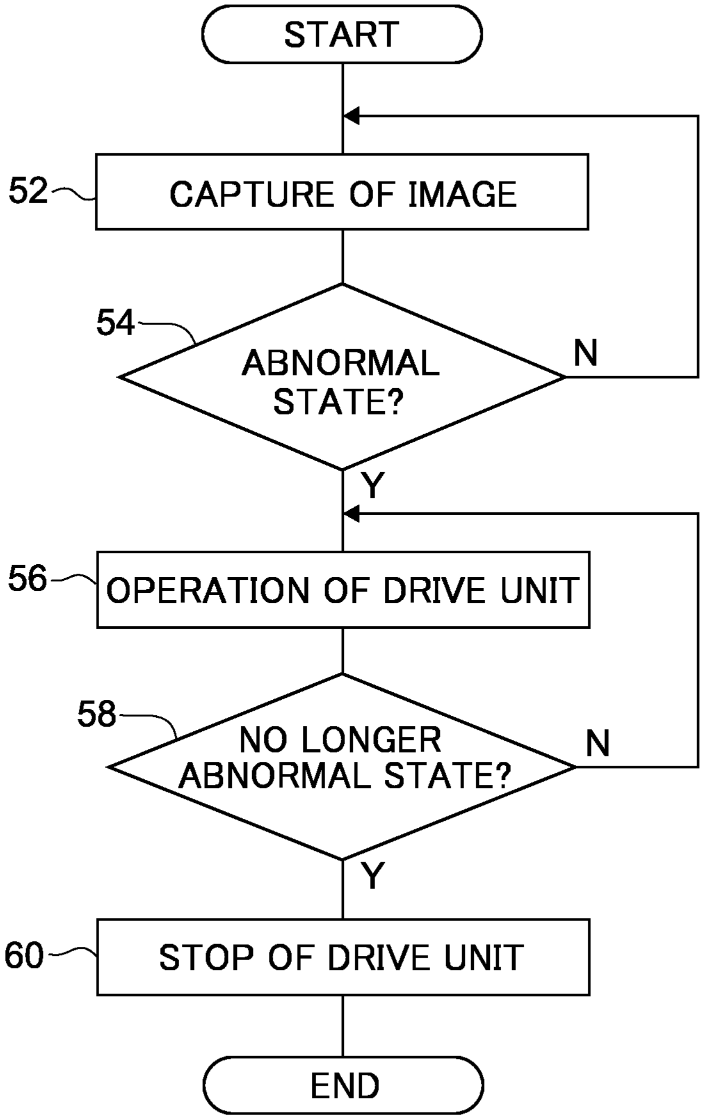
FIG. 3 is a flowchart of a bathtub drainage treatment program executed by a CPU 32 of the control device 30.

Next, the bathtub drainage treatment program executed by the CPU 32 of the control device 30 will be described with reference to FIG. 3.

When a switch (not shown) is turned on, the bathtub drainage treatment program is read from the ROM 34 or the storage device 44 into the RAM 36 and executed by the CPU 32, so as to execute the bathtub drainage treatment.

When the bathtub drainage treatment program is started, in step 52, the CPU 32 captures the image of the bather obtained by photographing the right side of the bathtub 12 in FIG. 1 with the camera 22.

In step 54, the CPU 32 determines whether or not the state of the bather is an abnormal state, based on a predetermined image of the abnormal state of the bather and the image of the bather obtained by photographing the right side of the bathtub 12 in FIG. 1 with the camera 22.

The predetermined image of the abnormal state of the bather is stored in the storage device 44. In step 54, the predetermined image of the abnormal state of the bather is read out from the storage device 44. The predetermined image of the abnormal state of the bather is, for example, an image in which the face, specifically, a nose of the bather is located at a position P1 below a liquid level of the hot water 20.

In step 54, the CPU 32 executes a process of matching the predetermined image of the abnormal state of the bather, read out from the storage device 44, with the image of the bather obtained by photographing the right side of the bathtub 12 in FIG. 1 with the camera 22, and calculates a matching ratio. When the matching ratio is equal to or higher than a predetermined value, the CPU 32 determines that the state of the bather is an abnormal state.

When it is not determined that the state of the bather is an abnormal state, the bathtub drainage treatment returns to step 52 and the above processes (that is, steps 52 and 54) are executed. When it is determined that the state of the bather is an abnormal state, the bathtub drainage treatment proceeds to step 56.

In step 56, the CPU 32 controls the drive unit 42 so as to operate so that the oil is supplied from the hydraulic circuit 18 to each hydraulic cylinder 16, in order to raise the plate 14 so that the opening is opened, and discharge, from the opening, the hot water 20 stored in the bathtub 12. When, in this way, the oil is supplied from the hydraulic circuit 18 to each hydraulic cylinder 16, each hydraulic cylinder 16 rises, the upper surface of each hydraulic cylinder 16 raises a portion of the rectangular plate 14, being inward at the predetermined distance from each corner thereof, and the plate 14 rises (see also FIG. 4).

When the plate 14 rises, the opening is opened, and the hot water 20 stored in the bathtub 12 is discharged from the opening as shown by the arrows F. When the hot water 20 stored in the bathtub 12 is discharged from the opening, the liquid level of the hot water 20 is lowered as shown by an arrow D.

By the way, the opening is opened because the plate 14 is raised. The buttocks of the bather are placed on the plate 14. When the plate 14 on which the buttocks of the bather are placed rises, the position of the bather, more specifically, the position of the face, particularly the nose and mouth of the bather, rises.

In step 58, the CPU 32 determines whether or not the state of the bather is no longer the abnormal state.

As described above, the hot water 20 stored in the bathtub 12 is discharged from the opening so that the liquid level of the hot water 20 is lowered as shown by the arrow D, and the plate 14 rises so that the position of the face, particularly the nose and mouth of the bather, rises as shown by an arrow U. When, in this way, the liquid level of the hot water 20 continues to be lowered and the position of the face, particularly the nose and mouth of the bather, continues to rise, after a certain period of time has elapsed from the start of the process of step 56, the position of at least the nose of the bather, being located at the position P1 below the liquid level of the hot water 20, has moved relatively to a position P2 above the liquid level of the hot water 20. When the position of at least the nose of the bather has moved to the position P2 above the liquid level of the hot water 20, the bather can breathe and is no longer in the abnormal state.

In step 60, the CPU 32 determines whether or not the certain period of time has elapsed from the start of the process of step 56 so as to determine whether or not the state of the bather is no longer the abnormal state. The certain period of time may be a time it takes for the positions of not only the nose but also the mouth to move to the position P2 above the liquid level of the hot water 20.

The technique of the present disclosure is not limited to determining whether or not the certain period of time has elapsed from the start of the process of step 56 so as to determine whether or not the state of the bather is no longer the abnormal state. For example, the CPU 32 may execute a process of matching the image obtained by the camera 22 with a predetermined image (stored in the storage device 44) of the case where the state of the bather is no longer the abnormal state, calculate the matching ratio, and determine that the state of the bather is no longer the abnormal state, when the matching ratio is equal to or higher than a predetermined value.

When it is not determined that the state of the bather is no longer the abnormal state, the bathtub drainage treatment returns to step 56, and the above processes (that is, steps 56 and 58) are executed. When it is determined that the state of the bather is no longer the abnormal state, the bathtub drainage treatment proceeds to step 60. In step 60, the CPU 32 stops the operation of the drive unit 42 and ends the bathtub drainage treatment.

As described above, in the present embodiment, when it is determined that the state of the bather is the abnormal state, in the state where the bather sits on the plate 14, the plate 14 is raised so that the opening is opened, and the hot water 20 stored in the bathtub 12 is discharged from the opening. Since, in this way, in the state where the bather sits on the plate 14, the plate 14 is raised so that the opening is opened, and the hot water 20 stored in the bathtub 12 is discharged from the opening, for example, in comparison with the case where the drain in the bathtub is merely unplugged, the liquid level of the hot water with respect to the face of the bather can be relatively lowered more quickly.

In the above-described embodiment, as the information indicating the state of the bather, the image of the face of the bather is acquired by photographing the bather with the camera 22, so as to determine whether or not the state of the bather is the abnormal state. The technique of the present disclosure is not limited to this. For example, a vital sensor that acquires vital signs (biological signals) of the bather may be used. The vital signs are, for example, heartbeat, respiration, blood pressure, pulse, body temperature and the like. According to the vital signs to be acquired, the vital sensor is attached to the body to acquire the vital signs, or is not attached to the body to acquire the vital signs in a non-contact manner. The CPU 32 determines whether or not the state of the bather is the abnormal state, based on the acquired vital signs and the values in the case where the state of the bather is the abnormal state.

Further, in the above-described embodiment, when it is determined that the state of the bather is the abnormal state, in the state where the bather sits on the plate 14, the plate 14 is immediately raised so that the opening is opened, and the hot water 20 stored in the bathtub 12 is discharged from the opening. However, the technique of the present disclosure is not limited to this. For example, a release button may be provided so that the press of the release button when the plate 14 starts to rise returns the rising plate 14 to the original position. Because, in reality, the bather may not be in the abnormal state.

What is claimed is:

1. A bathtub drainage device, comprising:

a plate, that can open and close an opening formed at a position corresponding to a position where a bather can sit on a floor of a bathtub in which hot water is stored, the plate on which at least buttocks of the bather can be placed;

a rising part, that raises the plate closing the opening so that the opening is opened;

an acquisition unit, that acquires information indicating a state of the bather; and a control unit, that controls the rising part so as to raise the plate so that the opening is opened and so as to discharge, from the opening, the hot water stored in the bathtub, when the information acquired by the acquisition unit indicates an abnormal state of the bather.

2. The bathtub drainage device of claim 1, wherein the control unit controls the rising part so that at least a nose of the bather is located above a surface of the hot water, when the information acquired by the acquisition unit indicates the abnormal state of the bather.

3. The bathtub drainage device of claim 1, wherein the acquisition unit is a photographing unit that acquires an image of the bather by photographing the bathtub, and the control unit determines whether or not the state of the bather is the abnormal state based on a predetermined image of the abnormal state of the bather and the image of the bather acquired by the photographing unit, and controls the rising part when the state of the bather is the abnormal state.

4. The bathtub drainage device of claim 1, wherein the acquisition unit is a vital sensor that acquires vital signs of the bather.

5. The bathtub drainage device of claim 1, further comprising a sealing member disposed between the opening and the plate.

* * * * *